US005774603A

United States Patent [19]

Moore et al.

[11] Patent Number: 5,774,603
[45] Date of Patent: Jun. 30, 1998

[54] OPTICAL CHEMICAL SENSOR

[75] Inventors: Christopher P. Moore, Harrow, United Kingdom; Jean C. Robert, Chalon-Sur-Saone, France; Robert G. Blue, Auldhouse; George Stewart, Ayrshire, both of Scotland

[73] Assignee: Eastman Kodak Company, Rochester, N.Y.

[21] Appl. No.: 811,086

[22] Filed: Mar. 3, 1997

[30] Foreign Application Priority Data

Mar. 2, 1996 [GB] United Kingdom .................... 9604542

[51] Int. Cl.$^6$ ......................................................... G02B 6/00
[52] U.S. Cl. ........................................... 385/12; 385/141
[58] Field of Search ............................... 385/12, 13, 128, 385/141

[56] References Cited

U.S. PATENT DOCUMENTS

| | | | |
|---|---|---|---|
| 4,600,310 | 7/1986 | Cramp et al. | 356/432 |
| 4,798,738 | 1/1989 | Yafuso et al. | 427/2 |
| 4,842,783 | 6/1989 | Blaylock | 264/1.1 |
| 4,886,338 | 12/1989 | Yafuso et al. | 350/96.29 |
| 5,137,560 | 8/1992 | Ohmura et al. | 65/60.52 |
| 5,244,636 | 9/1993 | Walt et al. | 422/82.07 |
| 5,280,548 | 1/1994 | Atwater et al. | 385/12 |
| 5,292,801 | 3/1994 | Avnir et al. | 525/54.1 |
| 5,300,564 | 4/1994 | Avnir et al. | 525/54.1 |
| 5,308,495 | 5/1994 | Avnir et al. | 210/656 |
| 5,371,018 | 12/1994 | Avnir et al. | 436/73 |
| 5,405,583 | 4/1995 | Goswami et al. | 422/86 |
| 5,501,836 | 3/1996 | Myerson | 422/57 |

FOREIGN PATENT DOCUMENTS

92/15862   9/1992   WIPO.

OTHER PUBLICATIONS

Wolfbeis, OS; "Analytical Chemistry With Optical Sensors" Apr. 1986, 325, pp. 387–392.

Seitz, WR; "Chemical Sensors Based On Immobilized Induciators and Fiber Optics", CRC Reviews in Analytical Chemistry, 19, Issue 2, 1988, pp. 135–173, no month.

Norris, OJW; "Current Status and Prospects for the Use of Optical Fibres In Chemical Analysis", Analyst, 114, Nov. 1989, pp. 1359–1372.

Zhengfang, G et al; "Fiber–Optic pH Sensor Based on Evanescent Wave Absorption Spectroscopy", Analytical Chemistry, 65, 1993, p. 2335 May.

Attridge, JW et al.; "Design of a Fibre–Optic pH Sensor With Rapid Response", J. Phys. E:Sci. Instrum., 20, p. 548 Aug. 1986.

Primary Examiner—John D. Lee
Assistant Examiner—Ellen E. Kang
Attorney, Agent, or Firm—John R. Everett

[57] ABSTRACT

An optical chemical sensor comprises an optical waveguide having a light transmitting substrate and a coating of an environmentally sensitive compound in a Zr/Si sol-gel glass binder on the substrate. The sensor is suitable for use in high pH environments. The environmentally sensitive compound may be a chemically sensitive dye e.g. a pH indicator dye.

12 Claims, 2 Drawing Sheets

OPTICAL CHEMICAL SENSOR

FIELD OF THE INVENTION

The invention relates to an optical chemical sensor suitable for use in high pH environments. More particularly, it relates to an optical chemical sensor comprising an optical waveguide having a light transmitting substrate and a coating of an environmentally sensitive compound e.g. a chemically sensitive dye in a binder on the substrate.

BACKGROUND OF THE INVENTION

Optical chemical sensors in which chemically sensitive dyes are used to sense the concentration of chemical species in the surrounding medium have been known for many years. For example, pH indicator dyes may be attached to an optical fiber and interrogated with light transmitted down the fiber, such that changes in pH are registered as a change in the spectral intensity of the light after modulation by the dye. Several comprehensive review articles on optical chemical sensing techniques exist in the literature, eg: Wolfbeis O S; "Analytical chemistry with optical sensors", Fresenius Z. Analytical Chemistry, 1986, 325, pp 387–392: Sietz W R; "Chemical sensors based on immobilized indicators and fiber optics", CRC Reviews in Analytical Chemistry, 19, Issue 2, 1988, pp 135–173: Norris J O W; "Current status and prospects for the use of optical fibres in chemical analysis", Analyst, 114, November 1989, pp 1359–1372.

Most of the activity in this field has been aimed at chemical sensing in non-hostile environments. For example a particular goal has been to use fiber optic chemical sensors for biosensing in which the environment is aqueous and close to neutral pH. Blood pH and dissolved oxygen sensors have been commercialised using immobilised dyes on very thin fiber optic probes. To date, very little work has been published dealing with optical chemical sensing in the more hostile high pH environments which are found, for example, in chemical manufacturing processes and photographic developer solutions.

In an optical fiber, the amplitude of the field does not drop abruptly to zero at the core/cladding boundary and a portion of energy extends a distance beyond the interface into the optically rarer medium. The field that penetrates is called the evanescent field and decreases exponentially in the direction of an outward normal to the boundary. The distance over which the evanescent field decays to 1/e or 37% of its value at the interface is called the penetration depth.

The existence of a continuous evanescent field along the fiber serves as a sensing area in which light travelling down the fiber core may be attenuated if it interacts with an absorber dye sited in the cladding. This is the principle of "evanescent wave sensing" which may be demonstrated using optical fibres or any other form of optical waveguide.

Examples of evanescent fiber optic pH sensing have been described. For example, Zhengfang G et al; 1993, Analytical Chemistry, 65, p2335, discloses the construction of a pH sensor based on a conductive polymer (polyaniline) coated on the core of an optical fiber, whilst Attridge J W et al, J. Phys. E: Sci. Instrum., 20, p548, discloses a coaxial directional coupler where refractive index changes in a polymer-dye composite causes light to couple to the second branch giving a measure of the pH change. Both these sensors are for use principally over the range pH 6–8.

WO 92/15862 discloses the use of sol-gel chemistry to form a thin film of inorganic silica-based glass containing the dye fluorescein over a 3 cm end portion of a short length of bare silica fiber core. Excitation of the dye at 488 nm by an argon ion laser generates fluorescence which travels in the opposite direction to the excitation light. After detection by photomultiplier, the sensor shows highest sensitivity to pH in the range pH 3.5–6.5.

Our research has shown that when conventional materials are used for immobilising chemically sensitive dyes as described in the published literature, the optical chemical sensors lack stability at high pH. Frequently, the coated layer in which the dye is immobilised is attacked and destroyed over relatively short time periods. Silica based sol-gel coatings used to trap chemically sensitive dyes suffer from degradation at high pH, eg: Douglas R W et al, Glass Technology, 1972, 13, p81: as do the core and cladding of unprotected silica optical fibres.

PROBLEM TO BE SOLVED BY THE INVENTION

The present invention overcomes the problem of the low stability of known optical chemical sensors in high pH environments.

SUMMARY OF THE INVENTION

The invention provides an optical chemical sensor comprising an optical waveguide having a light transmitting substrate and a coating of an environmentally sensitive compound in a binder on the substrate characterised in that the binder is a Zr/Si sol-gel glass.

The invention also provides a method of sensing a change in the chemical or physical properties of a fluid which comprises contacting the fluid with an optical chemical sensor according to the invention wherein the environmentally sensitive compound is sensitive to the change in the chemical or physical properties of the fluid, transmitting radiation through the sensor, and measuring the radiation which has been modified by or generated by the environmentally sensitive compound.

ADVANTAGEOUS EFFECT OF THE INVENTION

The optical chemical sensor of the invention can be used in the high pH environments which are found, for example, in chemical manufacturing processes and photographic developer solutions.

DETAILED DESCRIPTION OF THE INVENTION

Figure 1:
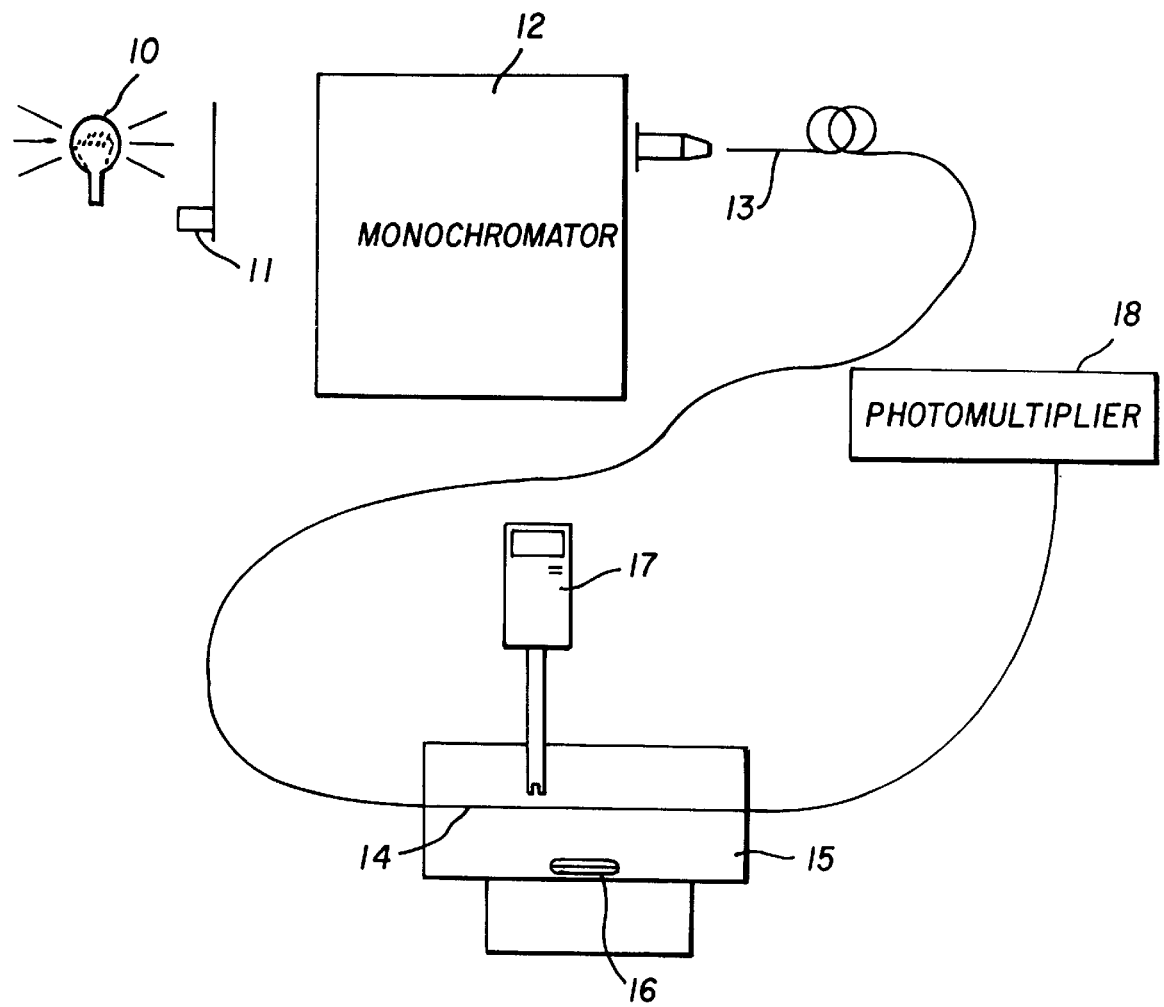
FIG. 1 is a schematic representation of apparatus using an optical chemical sensor of the invention.

The environmentally sensitive compound may be any compound which is sensitive to changes in the chemical or physical properties of the environment e.g. pH, humidity, temperature and pressure such that an optical property of the compound changes in response to a change in the environment. An example of an optical property which could change is the complex refractive index as a function of wavelength.

Examples of environmentally sensitive compounds include Nile Blue, calixarenes (e.g. Shinkai S. et al, Tetrahedron Letters, 33, 89, 1992), ruthenium complexes (e.g.

Moore P. et al, JCS Chem. Comm., 684, 1992), quinolines (e.g. Wollbeis O., Anal. Chem., 56, 4, 1984) and cobalt chloride. These compounds provide optical responses to protons, cations, copper, halide and humidity, respectively.

Preferably, the environmentally sensitive compound is a chemically sensitive dye.

The chemically sensitive dye may be any dye whose radiation absorption properties are altered by interaction with a chemical species to which the dye is sensitive. The chemically sensitive dye may be a fluorescent dye.

Examples of different classes of chemically sensitive dyes include pH sensitive dyes, cation sensitive dyes, anion sensitive dyes and molecular receptor bearing dyes.

In a preferred embodiment of the invention, the chemically sensitive dye is a pH sensitive dye. Examples of such dyes include Nile Blue, fluorescein, Oxazine 1 and bromocresol green.

The binder is a Zr/Si sol-gel glass. The preparation of inorganic e.g. silica glasses through the low temperature "sol-gel" synthesis is known. For example, see Chem. Rev. 1990, 90, 33–72 "The Sol-Gel Process" by L. L. Hench and J. K. West.

An amorphous matrix of the glassy material may be prepared by the room temperature polymerisation of suitable monomers, usually metal alkoxides. The polymerisation of metal alkoxide mixtures results in a transparent porous solid (xerogel) with surface areas of up to hundreds of square metres per gram and having small pores e.g. from 0.5 to 500 nm. The low temperature glass synthesis allows doping of the inorganic glass with organic molecules e.g. a chemically sensitive dye.

The sol-gel glass has a cage-like porous molecular structure in which a single doping molecule can be isolated in an individual cage, even at high concentrations of additive. Molecules trapped in sol-gel glasses can interact with diffusible solutes or components in an adjacent liquid or gas phase in the pore space.

Preferably, the mole percentage ratio of Zr to Si in the sol-gel glass is from 5:95 to 55:45, more preferably from 20:80 to 40:60.

The coating of the environmentally sensitive compound in the Zr/Si sol-gel glass binder may be provided along at least part of the length of the waveguide substrate to utilise the evanescent field of light transmitted in the waveguide.

Alternatively or additionally the coating may be provided at the end of the waveguide.

Alternatively the coating may modify the light transmission properties of the waveguide such that light propagates through the coating as well as the waveguide substrate.

The coating of the environmentally sensitive compound in the Zr/Si sol-gel glass binder may be a multilayer coating. Thicker coatings improve the containment of the evanescent field within the coating on the waveguide substrate and thus improve sensitivity and reduce possible unwanted interactions between the light and the bulk solution, especially those occurring at the interface between the coating and the bulk solution.

The waveguide substrate may be of an inorganic glass material, preferably a silica glass. Such substrates are in common use and are readily available.

The Zr/Si sol-gels exhibit good adhesion to waveguide substrates of either silica or higher index glasses. Furthermore, the coatings appear to retain the compound in such a way that it does not leach out gradually over time when the sensor is submerged in a fluid.

The waveguide may take any form e.g. planar, fiber, slab, disc, prism, strip, rod or film. In a preferred embodiment the waveguide is an optical fiber.

In the case of a planar waveguide, the light transmitting substrate usually comprises two contiguous layers, one layer having a higher refractive index than the other layer and guiding the light. The environmentally sensitive compound in a binder is present as a layer on top of the substrate which guides the light.

In the case of an optical libre, the light transmitting substrate is a fiber which guides the light and which is coated with the environmentally sensitive compound in a binder. The light guiding substrate may be referred to as the core and the coating may be referred to as the cladding.

An optical chemical sensor in accordance with the invention may be prepared by mixing a zirconium alkoxide, a silicon alkoxide and an environmentally sensitive compound in aqueous solution to fonn a sol, at least partially coating a waveguide substrate with the sol, and curing the at least partially coated waveguide substrate to convert the coating into a sol-gel glass.

The coating process may be repeated to produce a multilayer coating.

A zirconium alkoxide having the formula $Zr(OR)_4$ may be used wherein each R independently represents a straight or branched alkyl group having from 1 to 10 carbon atoms or an aryl group having from 1 to 10 carbon atoms. A preferred zirconium alkoxide is zirconium n-propoxide. The alkoxide is preferably present in an amount from 20 to 40 mol %.

A silicon alkoxide having the formula $Si(OR)_4$ may be used wherein each R independently represents a straight or branched alkyl group having from 1 to 10 carbon atoms or an aryl group having from 1 to 10 carbon atoms. A preferred silicon alkoxide is tetraethylorthosilicate. The alkoxide is preferably present in an amount from 60 to 80 mol %.

The pH of the alkoxide mixture is preferably less than 3 and more preferably in the range from 0.5 to 2.

A chemically sensitive dye may be present in an amount to give a final concentration from 00.1 mM to 100 mM, preferably from 0.01 to 50 mM.

Preferably, the mixture also contains one or more surfactants.

The waveguide substrate may be partially coated with the sol using any suitable technique e.g. dipping, spraying, casting and spin coating. In a preferred embodiment, the waveguide is an optical fiber which is coated by dipping the libre into a bath of the sol and withdrawing the coated fiber from the bath at a desired rate to fonn a desired thickness of coating on the fiber. Any cladding on the surface of the fiber to be coated is removed before coating so that the sol is deposited on the waveguide substrate.

The coating is preferably cured by heating at a temperature and for a time which are sufficient to produce the sol-gel glass e.g. at a temperature from 100° C. to 200° C. for a period from 8 hrs to 48 hrs. The temperature will be less than the dissociation temperature of the dye.

A method of sensing a change in the chemical or physical properties of a fluid e.g. a liquid or gas comprises contacting the fluid with an optical chemical sensor according to the invention wherein the environmentally sensitive compound is sensitive to the change in the chemical or physical properties of the fluid, transmitting radiation through the sensor, and measuring the radiation which has been modified by or generated by the environmentally sensitive compound.

For example, the method may be used to sense a chemical species in the fluid by using a dye which is sensitive to the chemical species and measuring the radiation which has been modified or generated by the interaction of the dye and the chemical species. The method may be qualitative or quantitative. In addition to indicating the presence of the chemical species, the method can indicate a property of the fluid e.g. pH.

The radiation transmitted through the optical waveguide preferably has a wavelength in the range from 200 nm to 5000 nm, preferably 350 nm to 1500 nm. Any suitable source of radiation may be employed such as an incandescent lamp, laser, laser diode or light emitting diode.

The radiation which has been modified by or generated by the environmentally sensitive compound can be measured in a number of known ways. For example, light intensity may be detected by conventional means including a photomultiplier tube, a photodiode, or other solid state detectors.

The optical chemical sensor of the invention is especially suitable for use in liquids having a high pH e.g. a pH greater than 9.

In a particular application, the optical chemical sensor is suitable for use in photographic developers which have pH values from about 9.5 to 12. A particular pH range of interest is 10 to 11.5 which covers most photographic developers.

The chemically sensitive dye may be a pH sensitive dye. A preferred dye for this use is Nile Blue which has approximately the right sensitivity range and has an absorption band in the red, enabling the use of cheap light sources such as LEDs or laser diodes. The sensor used in the Example below showed sensitivity to pH in the range 9 to 12.

The target chemical may be readily changed by substituting a different dye for Nile Blue. Sensing may be effected in both gases and liquids.

The invention is further illustrated by way of example as follows.

EXAMPLE 1

A mixture of tetraethylorthosilicate (1.4 eq, 15.96 ml), ethanol (26.1 eq, 76.8 ml) and water (1 eq, 0.9 ml) was transferred to ajar by a syringe equipped with a 0.5 micron filter in a clean room. The mixture was acidified to pH 1.5 by the addition of HCl, left to stir for 10 min and then placed in an ultrasound bath for 10 min. Zirconium(IV) n-propoxide (0.6 eq, 6.72 ml, 70 wt % solution in 1-propanol) was added slowly by similar syringe transfer. Finally, sufficient Nile Blue hydrochloride was added to give a final concentration of 0.001M in the solution; a surfactant, TX-100 (1 ml) was also added. Stirring was maintained for 5 min and then the mixture was placed in the ultrasonic bath for at least 2 hours. The sol was left to settle for approximately one week.

Plastic clad silica fiber with 200 micron diameter core was stripped over a 12 cm length approximately half way along an otherwise fully clad fiber. The sol was filtered into a bath and the fiber section was coated from this bath by immersing it in the bath and withdrawing it from the bath at a speed of 10 cm/min.

After coating, the fiber was quickly placed into an oven where the film underwent heat treatment at 130° C. for 24 hours. The coating process was then repeated until 6 coats had been applied. The coated fiber section was placed in a water-filled container and left to soak for approximately one week.

FIG. 1 illustrates the experimental set-up used to test the absorption characteristics of the dye in the sol-gel film. White light from an incandescent lamp 10 is passed through a light chopper 11 and then through monochromator 12 before being launched into the optical fiber 13.

The coated section 14 of the fiber i.e. the chemically sensitive part of the fiber, was immersed in water bath 15 provided with a magnetic stirrer 16 and a pH meter 17. The end of the optical fiber remote from the light source was connected to a photomultiplier tube 18 provided with means for lock-in detection referenced to the chopper frequency.

As the monochromator 12 was scanned across the wavelength range of interest, the transmitted light intensity was monitored using the photomultiplier tube 18. The pH of the water in the bath 15 was changed and the scanning process was repeated for several different pH values of the water surrounding the sensitive part of the libre. A further scan was made using an uncoated fully-clad fiber as a control.

Figure 2:
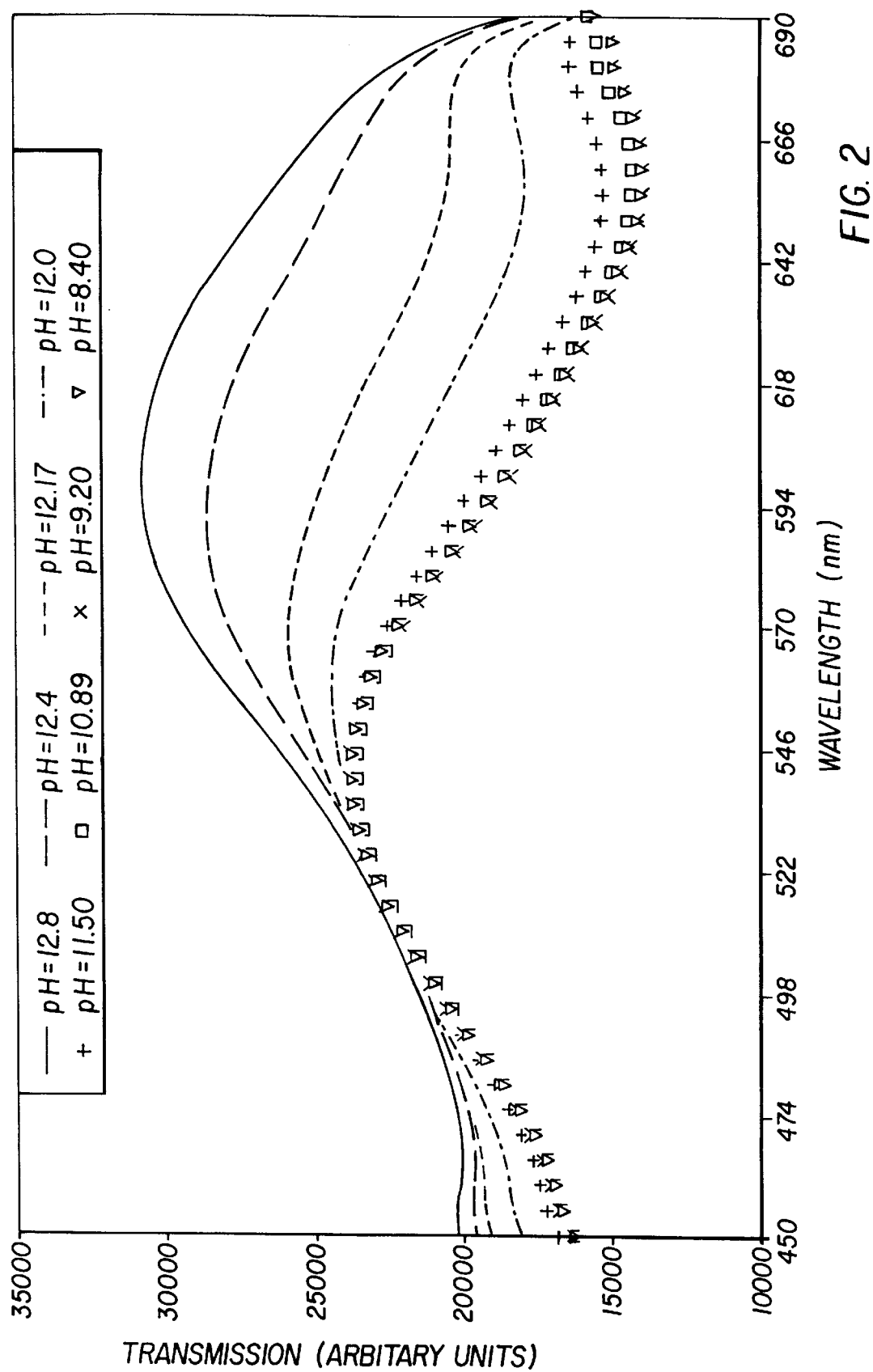
FIG. 2 is a graph showing the results obtained using an optical chemical sensor of the invention in accordance with Example 1 below.

The graph in FIG. 2 shows the response of the coated fiber in different pH solutions using the absorption sensing technique as described above.

Fluorescence sensing is also possible with Nile Blue. In that case, a He:Ne laser can be used to excite the dye and the fluorescence spectrum can be scanned as the pH is changed.

It has been further shown that coatings containing zirconium are stable towards high pH; exposure of these materials towards pH>13 has little or no effect after 3 weeks, whereas a similar coating made from tetraethylorthosilicate was largely decomposed within 48 hours.

In a commercial sensor, whole spectra need not be scanned. Instead two wavelengths alone could be used to both monitor intensity changes caused by pH shifts in the medium being sensed as well as drift due to the light source or dye loss by any mechanism. One of the two wavelengths would be selected to correspond to a wavelength band of minimum sensitivity to the chemical measurand of interest e.g. in FIG. 2 this band would be centred around 510 nm.

EXAMPLE 2

Experiments were carried out to demonstrate the alkaline durability of Zr/Si sol-gel films compared to films containing no Zr.

The Zr/Si sol-gel films were prepared on slides following the general preparative procedure given in Example 1. Zr content ranged from 0 to 70 mole %.

Buffer solutions were prepared and the exact pH was checked with a pH meter.

Batches of coated slides were placed onto slide racks and half of each slide was immersed lengthways into the buffer solution. The solutions were then sealed and left for a period of time after which the slides were examined.

Results achieved using different batches of slides are summarised as follows.

Batches 1 and 2

The slides were immersed for 24 hrs in pH 12.65 and 12.9 buffers. For high Zr content the films looked intact. For Zr content less than 30 mole % there appeared a faint dividing line along the length of the slide where it had been immersed in the liquid suggesting that the film had thinned slightly.

Batch 3

Films containing 0 mole % Zr and 30 mole % Zr were immersed for four days in pH 12.7 buffer. The 0 mole % Zr slides had a clear dividing line along them whereas the 30 mole % Zr slides appeared intact.

Batch 4

Slides having a variety of coated films were immersed for 24 hrs in a pH 13 buffer. 10 and 20 mole % Zr films were less damaged than the 0 mole % film. The 0 mole % Zr film had a prominent dividing line whereas a 30 mole % Zr film appeared intact.

Batch 5

Slides coated from 0 and 50 mole % Zr sols and dried at room temperature for 24 hrs were immersed for about 7 days in pH 10.66 buffer. The 0 mole % Zr films were completely removed from the slides. The 50 mole % Zr films remained on the slides.

Batch 6

Slides coated from 0 and 50 mole % Zr sols and dried at room temperature for 24 hrs were immersed for about 7 days in pH 9.62 buffer. The 0 mole % Zr films were completely or almost completely removed from the slides. The 50 mole % Zr films remained on the slides.

Batch 7

Slides coated from 0 and 50 mole % Zr sols and fired at 80° C. for 24 hrs were immersed for about 10 days in pH 9.6 buffer. The 0 mole % Zr films were completely or almost completely removed from the slides. The 50 mole % Zr films were intact.

Batch 8

Slides coated from 0 and 50 mole % Zr sols and fired at 80° C. for 24 hrs were immersed for about 10 days in pH 10.16 buffer. The 0 mole % Zr films were completely or almost completely removed from the slides. The 50 mole % Zr films were intact.

Batch 9

Slides coated from 0, 50 and 70 mole % Zr sols and fired at 80° C. for 24 hrs were immersed for about 10 days in pH 10.66 buffer. The 0 mole % Zr films were completely or almost completely removed from the slides. The 50 and 70 mole % Zr films were intact.

We claim:

1. An optical chemical sensor comprising an optical waveguide having a light transmitting substrate and a coating of an environmentally sensitive compound in a binder on the substrate characterised in that the binder is a Zr/Si sol-gel glass.

2. A sensor according to claim 1 wherein the mole percentage ratio of Zr to Si in the sol-gel glass is from 5:95 to 55:45.

3. A sensor according to claim 1 or claim 2 wherein the coating of the chemically sensitive dye in the Zr/Si sol-gel glass binder is provided along at least part of the length of the waveguide substrate.

4. A sensor according to claim 1 wherein the coating of the chemically sensitive dye in the Zr/Si sol-gel glass binder is a multilayer coating.

5. A sensor according to claim 1 wherein the waveguide substrate is of an inorganic glass material.

6. A sensor according to claim 5 wherein the waveguide is an optical fiber.

7. A sensor according to claim 1 wherein the environmentally sensitive compound is a chemically sensitive dye.

8. A sensor according to claim 7 wherein the chemically sensitive dye is a pH sensitive dye.

9. A sensor according to claim 8 wherein the chemically sensitive dye is Nile Blue.

10. A method of sensing a change in the chemical or physical properties of a fluid which comprises contacting the fluid with an optical chemical sensor according to claim 1 wherein the environmentally sensitive compound is sensitive to the change in the chemical or physical properties of the fluid, transmitting radiation through the sensor, and measuring the radiation which has been modified by or generated by the environmentally sensitive compound.

11. A method according to claim 10 of sensing a change in the pH of a fluid.

12. A method according to claim 10 or 11 wherein the pH of the fluid is greater than 9.

* * * * *